(12) United States Patent
Bourgeois et al.

(10) Patent No.: US 7,485,294 B2
(45) Date of Patent: Feb. 3, 2009

(54) GALENIC PECTINATE FORMULATION FOR COLON-TARGETED DELIVERY OF ANTIBIOTIC-INACTIVATING ENZYMES AND METHOD OF USE THEREOF

(75) Inventors: Sandrine Bourgeois, Paris (FR); Elias Fattal, Paris (FR); Antoine Andremont, Paris (FR); Patrick Couvreur, Villebon-sur-Yvette (FR)

(73) Assignee: Da Volterra (FR)

( * ) Notice: Subject to any disclaimer, the term of this patent is extended or adjusted under 35 U.S.C. 154(b) by 273 days.

(21) Appl. No.: 10/524,318

(22) PCT Filed: Aug. 6, 2003

(86) PCT No.: PCT/FR03/02474

§ 371 (c)(1),
(2), (4) Date: Feb. 9, 2005

(87) PCT Pub. No.: WO2004/016248

PCT Pub. Date: Feb. 26, 2004

(65) Prior Publication Data

US 2005/0249716 A1 Nov. 10, 2005

(30) Foreign Application Priority Data

Aug. 9, 2002 (FR) .................................. 02 10151
Oct. 29, 2002 (FR) .................................. 02 13514

(51) Int. Cl.
| | |
|---|---|
| C12N 9/00 | (2006.01) |
| C12N 9/14 | (2006.01) |
| C12N 9/18 | (2006.01) |
| A61K 38/43 | (2006.01) |
| A61K 38/46 | (2006.01) |
| A01N 63/00 | (2006.01) |

(52) U.S. Cl. .................... 424/94.1; 424/94.6; 424/93.1; 435/183; 435/195; 435/197

(58) Field of Classification Search ........................ None
See application file for complete search history.

(56) References Cited

U.S. PATENT DOCUMENTS

| | | | |
|---|---|---|---|
| 3,959,457 A | 5/1976 | Speaker et al. | |
| 5,607,671 A | 3/1997 | Heino | |
| 6,436,461 B1 * | 8/2002 | Bouwmeesters et al. | 426/575 |
| 6,500,423 B2 * | 12/2002 | Olshenitsky et al. | 424/93.3 |
| 6,531,152 B1 * | 3/2003 | Lerner et al. | 424/464 |
| 6,632,451 B2 * | 10/2003 | Penhasi et al. | 424/464 |
| 7,018,629 B2 * | 3/2006 | Jacob et al. | 424/93.48 |
| 2004/0067223 A1 * | 4/2004 | Jacob et al. | 424/93.48 |

FOREIGN PATENT DOCUMENTS

| | | | |
|---|---|---|---|
| EP | 0 213 303 A2 | | 3/1987 |
| EP | 0 338 499 A2 | | 10/1989 |
| EP | 0 480 729 A1 | | 4/1992 |
| JP | 04-013724 A | | 1/1992 |
| WO | WO 8807865 A | * | 10/1988 |
| WO | WO 92/00732 | | 1/1992 |
| WO | WO 93/13757 | | 1/1993 |
| WO | WO-95/05939 A1 | | 3/1995 |
| WO | WO-97/27843 A2 | | 8/1997 |
| WO | WO 98/15192 | * | 4/1998 |

OTHER PUBLICATIONS

Munjeri, O., et al. Journal of Pharmaceutical Sciences. 1998, 87(8), 905-908.*
Arthur, M. et al. "Heterogeneity of genes conferring high-level resistance to erythromycin by inactivation in enterobacteria" Annales de l'institut Pasteur, Microbiologie. 137(1.1) Jan./Feb. 1986, pp. 125-134. (Abstract Only).*
Ounissi, H. and Courvalin, P. "Nucleotide sequence of the gene ereA encoding erythromycin esterase in *E.coli*", Gene.1985, 35(3), pp. 271-278. (Abstract Only).*
Noguchi, N., et al. "Regulation of Transcription of the mph(A) Gene for Macrolide 2'-Phosphotransferase I in *Escherichia coli*: Characterization of the Regulatory Gene mphR(A)" Journal of Bacteriology. 2000, 182(18), 5052-8.*
Mathiowitz, E. "Oral Drug delivery, Small Intestine & Colon", Encyclopedia of Controlled Drug Delivery, vols. 1-2. 1999, pp. 717-728.*
Leonard F., et al., "Use of Beta-Lactamase-producing Anaerobes to prevent Ceftriaxone from Degrading Intestinal Resistance to Colonization" J. Infectious Disease. 1989, 160(2), 274-280 (Cas Abstract).*
Aydin, Z. and Akbuga, J., "Preparation and evaluation of pectin beads", *Inter. J. Pharm.*, v. 137, p. 133-136, 1996.
Krishnaiah, Y.S.R., et al., "Evaluation of guar gum as compression coat for drug targeting to colon", *Inter. J. Pharm.*, v171, p. 137-146, 1998.
Milojevic, S., et al., "Amylose as a coating for drug delivery to the colon: Preparation and in vitro evaluation using 5-aminosalicylic acid pellets", *J. Cont. Release*, v37, p. 75-84, 1996.
Munjeri, O., et al., "Hydrogel beads based on amidated pectins for colon-specific drug delivery: the role of chitosan in modifying drug release", *J. Cont. Release*, v46, p. 273-278, 1997.
Rubinstein, A., et al., "In Vitro Evaluation of Calcium Pectinate: A Potential Colon-Specific Drug Delivery Carrier", *Pharm. Res.*, v.10:2, p. 258-263, 1993.
Rubinstein, A., et al., "Colonic Drug Delivery: Enhanced Release of Indomethacin from Cross-Linked Chondroitin matrix in Rat Cecal Content", *Pharm. Res.*, v9:2, p. 276-278, 1992.
Sriamornsak, P., "Investigation of pectin as a carrier for oral delivery of proteins using calcium nectinate gel beads", *Inter. J. Pharm.*, v169, p. 213-220, 1998.
Sriamornsak, P., "Effect of calcium concentration, hardening agent and drying condition on release characteristics of oral proteins from calcium pectinate gel beads", *Eur. J. Pharm. Sci.*, v8, p. 221-227, 1999.
Wakerly, Z., et al., "Pectin/Ethylcellulose Film Coating Formulations for colonic Drug Delivery", *Pharm. Res.*, v13:8, p. 1210-1212, 1996.

* cited by examiner

*Primary Examiner*—Sandra Saucier
*Assistant Examiner*—Aaron J Kosar
(74) *Attorney, Agent, or Firm*—David Bradin; Intellectual Property/ Technology Law

(57) ABSTRACT

Forms of colonic delivery suited to be used orally and designed for colonic delivery of active ingredients selected from the group comprising enzymes capable of inactivating macrolide antibiotics and related compounds, enzymes capable of inactivating quinolones, and β-lactamases.

14 Claims, 8 Drawing Sheets

Whole Beads

Cut Beads

Whole Beads

Cut Beads

Whole Beads

Cut Beads

Whole Beads

Cut Beads

GALENIC PECTINATE FORMULATION FOR COLON-TARGETED DELIVERY OF ANTIBIOTIC-INACTIVATING ENZYMES AND METHOD OF USE THEREOF

FIELD OF THE INVENTION

The present invention relates to a galenic form for colon-targeted delivery, its preparation process and its use in therapeutic.

The present application is a national phase entry of PCT WO 2004/016248 A2, filed on Aug. 6, 2003, which itself claims priority to French Application 02/10151, filed on Aug. 9, 2002, and French Application 02/13514, filed on Oct. 29, 2002, the contents of each of which are incorporated by reference in their entirety.

BACKGROUND OF THE INVENTION

Specific release systems in the colon have been proven to have significant theracanic advantages.

A large number of colonic illnesses could effectively be treated more efficaciously if the active ingredient were released locally. This is the case, inter alia, for Crohn's disease, ulcerative colitis, colorectal cancer and constipation.

Colon-targeted release could also be interesting when, from the theracanic point of view, a delay in absorption is necessary, in particular in the treatment of pathologies such as nocturnal asthma or angor (Kinget R. et al. (1998), Colonic Drug Targeting, Journal of Drug Targeting, 6,129).

The administration of polypeptidic active ingredients occurs essentially parenterally, which is painful and the origin of poor observation of treatment. For some years now there has been an interest in using the colon as an absorption site for peptidic active ingredients (analgesic, contraceptive, vaccine, insulin . . . ). The absorption of peptides in the colon seems effectively better than at other sites of the digestive tract, in particular due to proteolytic activity clearly weaker than in the small intestine and in the absence of peptidasic activity associated with the membrane of the epithelial colonic cells.

During oral administration of antibiotics, these pass through the stomach and are then absorbed in the small intestine to diffuse in the entire organism and treat the infectious focus for which they have been administered. All the same, a fraction of ingested antibiotics (whereof the importance varies with the characteristics peculiar to each type of antibiotic) is not absorbed and continues its progress to the colon before being eliminated in the stool. These residual antibiotics are reunited, in the small intestine, by a fraction of the antibiotics absorbed, but which are re-excreted in the digestive tract by way of biliary elimination. This fraction is of variable importance as a function of metabolism and elimination paths of each antibiotic. Finally, for certain antibiotics, a fraction of the dose absorbed is eliminated directly by the intestinal mucous in the lumen of the digestive tract. Since the antibiotics had been administered orally or parenterally, an active residual fraction is generally found in the colon. This holds true, to varying degrees, for the vast majority of the families of antibiotics utilised in therapeutics, the only notable exception being the family of amino-glycosides for which intestinal excretion is negligible. For the other antibiotics, intestinal excretion of a residual antibiotic activity will have different consequences, all harmful. In effect, in the colon there is a complex (several hundreds of different bacterial species) and very dense (more than $10^{11}$ bacteria per gram of colonic content) bacterial ecosystem which will be affected by the arrival of active residues of antibiotics. The following is observed:

1) imbalance of flora which would be the main cause of banal diarrhoea sometimes following ingestion of antibiotics (Bartlett J. G. (2002) Clinical practice. Antibiotic associated diarrhea, New England Journal of Medicine, 346, 334). Even though this diarrhoea is generally not serious and quickly abates, either spontaneously, or when treatment is discontinued, it is nevertheless badly received by patients and adds to the discomfort of the basic illness for which antibiotics have been prescribed;

2) perturbation of the functions of resistance to colonisation by exogenic bacteria (or "barrier effect") with the possibility of increased risk of infection, for example, alimentary intoxication to *Salmonella* (Holmberg S. D. et al. (1984) Drug resistant *Salmonella* from animals fed antimicrobials, New England Journal of Medicine, 311, 617);

3) selection of micro-organisms resistant to antibiotics. The latter can be of various types:

a) they can first be pathogenic bacteria, such as for example *Clostridium difficile*, a species capable of secreting toxins causing redoubtable colitis known as pseudomembranous (Bartlett J. G. (1997) Clostridium difficile infection: pathophysiology and diagnosis, Seminar in Gastrointestinal Disease, 8,12);

b) they can also be relatively slightly pathogenic microorganisms but whereof the multiplication can lead to surrounding infection (vaginal *Candidosis* or *Escherichia coli* resistant cystitis).

c) they can finally be non-pathogenic commensal resistant bacteria but whereof the multiplication and faecal elimination will boost dissemination in the environment. As it is, these resistant commensal bacteria can constitute an important source of resistance mechanisms for pathogenic species. This risk is currently considered to be major in terms of the worrying character in the evolution to multiresistance of numerous pathogenic species for humans.

Numerous strategies exploiting the diverse physiological parameters of the digestive tract have therefore been envisaged with a view to releasing active ingredients in the colon. Studies have in particular been carried out by means of administration systems based on (1) utilisation of polymers sensitive to variations in pH, (2) release forms dependent on time, (3) prodrugs or again polymers degradable by bacteria in the flora.

(1) Systems Based on Variations in pH.

The pH in the stomach is of the order of 1 to 3 but it increases in the small intestine and colon to reach values close to 7 (Hovgaard L. et al. (1996) Current Applications of Polysaccharides in Colon Targeting, Critical Reviews in Theracanic Drug Carrier Systems, 13,185). For an active ingredient to reach the colon, without undergoing these variations in pH, it is possible to administer it in the form of tablets, gels or spheroids coated in a pH-dependent polymer, insoluble in acid pH but soluble in neutral or alkaline pH (Kinget et al. op cit). The most commonly used polymers are derivatives of methacrylic acid, Eudragite L and S (Ashford M. et al. (1993), An in vivo investigation into the suitability of pH-dependent polymers for colonic targeting, International Journal of Pharmaceutics, 95,193 and 95,241; and David A. et al. (1997) Acrylic polymers for colon-specific drug delivery, S.T.P. Pharma Sciences, 7, 546).

Given the important inter- and intra-individual variability of the values of pH at the gastro-intestinal tract level, pH-dependent polymers do not represent the best means for obtaining specific release in the colon (Ashford M. et al., op cit.).

(2) Systems Based on Transit Time.

The formulation of these systems is such that it allows release of the active ingredients after a predefined lag time. So as to release the active ingredient in the colon, these forms must still resist the acid environment of the stomach and enter a silent phase of a predetermined time, before releasing the active ingredient, corresponding to the transit time from the mouth to the terminal ileon (Gazzaniga A. et al. (1995) Time-dependent oral delivery systems for colon targeting, S.T.P. Pharma Sciences, 5,83 and 108, 77; Liu P. et al. (1999) Alginate/Pectin/Poly-L-lysine particulate as a potential controlled release formulation, J. Pharm. Pharmacol., 51, 141; Pozzi F. et al. (1994) The Time Clock system: a new oral dosage form for fast and complete release of drug after pre-determined lag time, Journal of Controlled Release, 31,99).

Pulsincap® by Scherer was one of the first formulations of this type (international patent application WO90/09168). It has the appearance of a gel whereof the body is insoluble in water. The active ingredient is maintained in the body by a hydrogel stopper placed in the head of the hydrosoluble gel. The whole is coated in a gastro-resistant film. After dissolution of the head in the small intestine, the stopper swells on contact with digestive juices. When the latter reaches a critical swelling threshold it is ejected, thus allowing release of the active ingredient. The ejection time is controlled by the properties of the hydrogel constituting the stopper.

Systems based on transit time nevertheless offer numerous disadvantages (variations in time for emptying of stomach and transit time, retention phenomena in the ileo-caecal valve (Kinget R., op. cit.), causing a lack in specificity and preventing validation of the latter as specific release systems in the colon. Finally, large-scale production of this type of system is difficult to envisage, as this would require and costly significant adaptation of industrial technologies.

Recently a novel form for colonic targeting has been developed, "Colon-targeted Delivery Capsule" (CTDC) (Ishibashi T. et al. (1998) Design and evaluation of a new capsule-type dosage form for colon-targeted delivery of drugs, International Journal of Pharmaceutics, 168,31 and 57,45). The CTDC is a system bringing together the pH-dependent factor and the time-dependent factor. It is in the form of a classic gel encasing the active ingredient and an organic acid (succinic acid), covered in 3 layers.

(3) Systems Based on Enzymatic Activity of the Microbial Colonic Flora.

3.1. Prodrugs.

Prodrugs have largely been studied for colonic targeting of various active ingredients (anti-inflammatory non-steroidal and steroidal, spasmolytic, . . . ). These systems are based on the capacity of the enzymes produced by the colonic flora for degrading prodrugs in order to release the active form of the active ingredient.

Numerous prodrugs based on the action of the bacterial azoreductases in particular have been developed with the aim of releasing in the colon active ingredients such as 5-aminosalicylic acid (5-ASA) utilised in the treatment of local pathologies such as Crohn's disease or ulcerative colitis (Peppercorn M. A. (1972) The role of intestinal bacteria in the metabolism of salicylazosulfapyridine, The Journal of Pharmacology and Experimental Therapeutics, 181, 555 and 64, 240).

Another approach consists of exploiting bacterial hydrolases such as glycosidases and polysaccharidases (Friend D. R. (1995) Glycoside prodrugs: novel pharmacotherapy for colonic diseases, S.T.P. Pharma Sciences, 5, 70 Friend D. R. et al. (1984) A colon-specific drug-delivery system based on drug glycosides and the glycosidases of colonic bacteria, Journal of Medicinal Chemistry, 27, 261; Friend D. R. et al. (1985) Drug glycosides: potential prodrugs for colon-specific drug delivery, Journal of Medicinal Chemistry, 28, 51; and Friend D. R. et al. (1992) Drug glycosides in oral colon-specific drug delivery, Journal of Controlled Release, 19, 109). Prodrugs have thus been developed by coupling, for example, steroids to sugars (glucose, galactose, cellobiose, dextran (international patent application WO90/09168)), cyclodextrins (Hirayama F. et al. (1996) In vitro evaluation of Biphenylyl Acetic Acid-p-Cyclodextrin conjugates as colon-targeting prodrugs: drug release behavior in rat biological media, Journal of Pharmacy and Pharmacology, 48, 27).

3.2. Coating by Polymers Biodegradable by Bacterial Enzymes.

In this case, colonic targeting is done by coating the pharmaceutical form with a polymer specifically degraded by the enzymes produced by microflora, by benefiting from the presence of azoreductases or bacterial glycosidases.

Numerous polymers including azoaromatic links have been used to coat an active ingredient. Saffran et al. (Oral insulin in diabetic dogs, Journal of Endocrinology (1991), 131, 267 and A new approach to the oral administration of insulin and other peptide drugs, Science (1986), 233, 1081) have described the release of insulin and vasopressin in the colon of rats and dogs from oral forms coated with copolymers of styrene and hydroxyethylmethacrylate (HEMA) linked by azoaromatic bonds. This coating is degraded in the colon by bacterial azoreductases responsible for release of the active substance.

The advantage of azopolymers is that they allow very good colonic selectivity for release of active ingredients. The disadvantage associated with use is the lack of information on their possible toxicity.

To avoid this disadvantage, other studies have chosen to focus on the use of coating film based on natural substance such as polysaccharides in particular with coating films based on amylose/ethylcellulose (Milojevic S. et al. (1996) Amylose as a coating for drug delivery to the colon: preparation and in vitro evaluation using 5-aminosalicylic acid pellets, Journal of Controlled Release, 38, 75), based on dextrane ester (Bauer K. H. et al. (1995) Novel pharmaceutical excipients for colon targeting, S.T.P. Pharma Sciences, 5, 54) or pectin.

3.3. Matrices Biodegradable by Bacterial Enzymes.

Another approach of systems of specific release in the colon consists of the elaboration of matrices by compression of a mixture of active ingredient and biodegradable polymers such as chondroitin sulfate (Rubinstein A. et al. (1992b) Chondroitin sulfate: a potential biodegradable carrier for colon-specific drug delivery, International Journal of Pharmaceutics, 84, 141 and Rubinstein A. et al. (1992a) Colonic drug delivery: enhanced release of Indomethacin from cross-linked chondroitin matrix in rat cecal content, Pharmaceutical Research, 9,276), guar gum (Krishnaiah Y. S. R. et al. (1998) Evaluation of guar gum as a compression coat for drug targeting to colon, International Journal of Pharmaceutics, 171, 137), chitosan (Tozaki H. et al. (1997) Chitosan capsules for colon-specific drug delivery: improvement of insulin absorption from the rat colon, Journal of Pharmaceutical Sciences, 86,1016) or pectin (Rubinstein A. et al. (1993) In vitro evaluation of calcium pectinate: a potential colon-specific drug delivery carrier, Pharmaceutical Research, 10, 258).

Systems based on enzymatic activity of microbial flora are probably those having the greatest colonic specificity for release of the active ingredients. Therefore they make up a future path for colonic targeting.

The interest in polysaccharides in the preparation of systems for colonic administration is that they are of natural origin, only slightly toxic and specifically degraded by bacterial enzymes of the colonic flora.

Thus, pectin is a polysaccharide isolated from the cellular walls of superior vegetables, widely used in the agro-alimentary industry (as a gelling agent or thickener of jams, ices . . . ) and pharmaceutical. It is polymolecular and polydisperse. Its composition varies according to the source, conditions of extraction and environmental factors.

Pectins are principally composed of linear chains of acids α-1,4-(D)-galacturonic, sometimes interspersed with units of rhamnose. The carboxylic groups of galacturonic acids can be partially esterified to give methylated pectins. Two types of pectin are distinguished according to their degree of methylation (DM: number of methoxy group per 100 units of galacturonic acid):

highly methylated pectin (HM: high methoxy) whereof the degree of methylation varies between 50 and 80%. It is only slightly soluble in water and form gels in an acid medium (pH<3.6) or in the presence of sugars;

slightly methylated pectin (LM: low methoxy), with a degree of methylation from 25 to 50%. More soluble in water than HM pectin, it gives gels in the presence of divalent cations such as $Ca^{2+}$ ions. In fact, Ca2+ ions form "bridges" between carboxylated groups free of galacturonic acids. The network thus formed has been described by Grant et al. Under the name of egg-box model (Grant G. T. et al. (1973) Biological interactions between polysaccharides and divalent cations: the egg-box model, FEBS Letters, 32, 195).

There are also amidated pectins. Certain groups of methyl carboxylate ($-COOCH_3$) can be transformed into carboxamide groups ($-CONH_2$) by treatment of pectin by ammonia. This amidation imparts novel properties to the pectins, in particular improved resistance to variations in pH.

The pectin is degraded by enzymes originating from superior vegetables and diverse micro-organisms (mushrooms, bacteria . . . ) including bacteria of human colonic flora. The enzymes produced by the microflora are composed of polysaccharidases, glycosidases and esterases.

A galenic form is coated by pectin either via compression (Ashford M. et al. (1993b), An evaluation of pectin as a carrier for drug targeting to the colon, Journal of Controlled Release, 26, 213), or by pulverisation. Coating by compression is generally completed with pectin alone, whereas compression by pulverisation requires the use of a filmogenic polymer in addition to the pectin (Milojevic S. et al. (1996) Amylose as a coating for drug delivery to the colon: preparation and in vitro evaluation using 5-aminosalicylic acid pellets, Journal of Controlled Release, 38, 75; Wakerly Z. et al. (1996) Pectin/ethycellulose film coating formulations for colonic drug delivery, Pharmaceutical Research, 13, 1210).

Numerous matricial forms based on pectin have likewise been studied. They are generally constituted either by pure pectin, or by its complex with $Ca^{2+}$ ions, slightly hydrosoluble, calcium pectinate. A matrix of calcium pectinate including indomethacin has in particular been described by Rubinstein et al. (1992a) Colonic drug delivery: enhanced release of Indomethacin from cross-linked chondroitin matrix in rat cecal content, Pharmaceutical Research, 9, 276) showing better stability of the calcium pectinate than the pectin alone in digestive juices, while remaining sensitive to the action of pectinolytic enzymes.

The amidated pectins, more tolerant to variations in pH have also been studied for elaboration of matricial tablets for colonic observation (Wakerly Z. et al. (1997) Studies on amidated pectins as potential carriers in colonic drug delivery, Journal of Pharmacy and Pharmacogyl. 49, 622).

Aydin et al.( (1996) Preparation and evaluation of pectin beads, International Journal of Pharmaceutics, 137,133) were the first to formulate pectin beads according to the ionic gelification method by Bodmeier et al. ((1989) Preparation and evaluation of drug-containing chitosan beads, Drug Development and Industrial Pharmacy, 15, 1475 and Spherical agglomerates of water-insoluble drugs, Journal of Pharmaceutical Sciences, 78, 964), who had disclosed beads of alginate and chitosan. Their objective was to incorporate in the beads two different active ingredients, a cationic (atenolol) and an anionic (piroxicam), so as to characterise possible interactions with pectin. They have thus demonstrated that it was possible to form beads with the 2 types of active ingredients and that the operational conditions had a major influence on the properties of the resulting beads.

Sriamornsak used beads of calcium pectinate to establish a system for specific release of proteins in the colon, by using bovine serum albumin (BSA) having a molecular weight of 66400 Da as protein model (Sriamornsak P. (1998) Investigation on pectin as a carrier for oral delivery of proteins using calcium pectinate gel beads, International Journal of Pharmaceutics, 169, 213 and (1999) Effect of calcium concentration, hardening agent and drying condition on release characteristics of oral proteins from calcium pectinate gel beads, European Journal of Pharmaceutical Sciences, 8, 221). He studied the influence of different factors of formulation on the properties of the resulting beads, such as their form, their size, the rate of encapsulation of the BSA and its release kinetics. Sriamornsak has therefore demonstrated that the pectinate beads of Ca could be employed for specific release of proteins in the colon. Obtaining an adequate release kinetic profile depends principally on the choice of the formulation and operational conditions for preparation of the beads. No in vitro/in vivo correlation of the release profiles of the encapsulated active ingredients has been established.

To boost the stability of the particles along the digestive tract and to avoid any premature release of the encapsulated active ingredient, it is possible to reinforce the pectin beads by reticulating them with a cationic polymer.

Munjeri et al.( (1997) Hydrogel beads based on amidated pectins for colon-specific drug delivery: the role of chitosan in modifying drug release, Journal of Controlled Release, 46, 273) have reticulated pectin beads amidated with chitosan. They then showed, by comparing the kinetics of dissolution of reticulated forms and of non-reticulated forms, that the chitosan allowed the release of the active insoluble ingredients to be minimised, but did not significantly modify the release of the hydrosoluble active ingredients. The loss of active ingredient in conditions emulating those of the stomach and the small intestine can therefore be limited by formation of a complex between the chitosan and the amidated pectin; the reticulated pectin beads still remain sensitive to the action of the colonic pectinolytic enzymes.

Another reticulating agent, polylysine, has been tested in the presence of alginate/pectin beads (Liu P. et al. (1999) Alginate/Pectin/Poly-L-lysine particulate as a potential controlled release formulation, J. Pharm. Pharmacol., 51,141). The beads reticulated by the polylysine seem to release less active ingredient in an acid medium (HCl O,1N) than the non-reticulated beads, except in the presence of highly hydrosoluble active ingredients. The same type of effect is found in an alkaline medium (phosphate buffer, pH 7.5) but it is clearly less marked than in acid medium.

International patent application WO 88/07865 suggests administering bacteria producing β-lactamases in the colon so as to hydrolyse the residual antibiotics. The micro-organisms utilised are bacteria with strict anaerobic metabolism, whereof the production and lyophilisation in sufficient quantity to make a drug are difficult. Furthermore, they are carriers of genes resistant to the antibiotics encoding for β-lactamases thus engendering a risk of dissemination of these genes within the colonic ecosystem and in the environment.

International patent application WO 93/13795 proposes an oral galenic form containing β-lactamases. It can be composed of saccharose particles of 1 to 2.5 mm in diameter enclosing the β-lactamases or amidase and optionally an inhibitor of trypsine, said particles being covered by a gastroresistant polymer. These particles could well release the enzyme in different segments of the digestive tract so that its activity takes place as required at the desired site in the intestine.

None of the examples comprises experimental data showing that the proposed galenic formulation is effectively capable of releasing the enzyme in an active form at the desired site in the intestine. In addition, no proof of the capacity of galenic preparation for effectively hydrolysing the antibiotic in vivo, nor even in vitro in a medium reproducing the characteristics of the intestinal medium is given.

For all these reasons, it is highly desirable to use a system for reducing the quantity of residual antibiotics which reach the colon after oral or parenteral antibiotherapy, or capable of delivering an active ingredient directly to the colon.

Therefore, the object of the present invention is multiparticular galenic forms to be utilised orally and for colonic delivery of active ingredients.

SUMMARY OF THE INVENTION

In the sense of the present invention, active ingredient is understood to mean a substance or composition which is suitable to be utilised in therapeutics or in diagnostics and can be incorporated in the galenic form according to the invention.

The active ingredient can be an anti-infectious, for example antibiotics, anti-inflammatory compounds, anti-histamines, anti-cholinergics, antivirals, antimitotics, peptides, proteins, genes, anti-sense oligonucleotides, diagnostic agents and/or immunosuppressive agents or bacteria.

Examples of particularly advantageous active ingredients are anti-inflammatory agents, antitumoral agents, anti-sense oligonucleotides and enzymes capable of inactivating antibiotics in the colon, in particular β-lactamases or enzymes capable of inactivating macrolids and related substances, such as erythromycin esterase described by Andremont A. et al.((1985) Plasmid mediated susceptibility to intestinal microbial antagonisms in *Escherichia coli* Infect. Immun. 49 (3), 751) or capable of inactivating quinolones such as those described by Chen Y et al.( (1997) Microbicidal models of soil metabolisms biotransformations of danofloxacin, Journal of Industrial Microbiology and Biotechnology 19,378).

The active ingredients can be hydrosoluble or liposoluble.

In an advantageous embodiment of the invention, the multiparticular galenic forms suitable to be utilised orally and for colonic delivery of active ingredients comprise pectin beads in the form of a cationic salt enclosing the active ingredient, said pectin being reticulated by a cationic polymer.

In an advantageous embodiment according to the invention the cationic polymer which allows reticulation of the pectin is selected from the group composed of polyethylenimine, polylysine, chitosan and their derivatives.

More advantageously, the molecular weight of these cationic polymers, is between 10,000 and 100,000 Daltons, preferably between 20,000 and 50,000 Daltons.

In another advantageous embodiment of the invention, the cationic pectin salt used is calcium pectinate. In the sense of the present invention, pectin is also understood to mean methylated or non-methylated, amidated or non-amidated pectin.

The galenic forms according to the invention can be administered in all oral forms, in particular in the form of gels and capsules.

These gels and these capsules can be administered simultaneously or successively with other active ingredients, in particular when the gels or the capsules contain enzymes capable of inactivating the antibiotics, they can be administered simultaneously or successively with the preparation of corresponding antibiotics.

The active ingredients administered conjointly with the gels and capsules containing the galenic forms according to the invention are administered orally or via any other method.

The galenic forms according to the invention can be prepared by methods known to the expert or by novel processes which likewise make up part of the invention.

Accordingly, the object of the present invention is also a process for preparation of multiparticular galenic forms, characterised in that an aqueous solution of pectin containing the active ingredient is added dropwise to a concentration of 0.5 to 5% (v/v) in a solution of calcium chloride to form the beads of calcium pectinate, then the beads of calcium pectinate thus obtained are recovered and introduced to an aqueous solution of the polymer cationic.

In an advantageous embodiment of the process, the pectin solution is 4 to 10% (m/v), preferably 4 to 7%, the solution of calcium chloride from 2 to 10% (m/v) and the solution of polymer cationic from 0.5 to 2% (m/v), said solution of polymer cationic preferably being a solution of polyethylenimine.

In an even more advantageous embodiment of the invention the galenic forms are prepared from a solution of pectin at 6% (m/v), a solution of calcium chloride at 6% (m/v) and a solution of polyethylenimine at 1% or at 0.6%.

The beads are maintained in the calcium chloride with slow stirring for 10 min to 1 hour, preferably for 20 min. The reticulation stage by the cationic polymer is performed with slow stirring for 15 to 40 min, preferably for 20 min.

After recovery of the pectinate beads, the beads are dried at a temperature of between 20 and 40° C. for 30 min to 10 hours, preferably at 37° C. for 2 hours.

The diameter of the particles according to the invention is between 800 and 1500 μm, preferably between 1000 and 1200 μm.

The encapsulation yields are between 50 and 90% or 3-6 UI/beads of β-lactamases, activity expressed in the benzylpenicillin substrate, whether the pectin is amidated or not.

Stability in gastric juice is greater than 10 hours and is likewise very good in intestinal medium USP XXIV, since it is greater than 7 hours (the duration of stability of non-reticulated pectin beads does not exceed 1 hour) and this irrespective of the type of pectin utilised.

Examples 1 to 7 and FIGS. 1 to 8 which follow illustrate the invention.

DETAILED DESCRIPTION OF THE INVENTION

The following examples are provides to further illustrate the present invention, and Should not be construed as limiting thereof.

EXAMPLE 1

Preparation of Galenic Forms

An aqueous solution of pectin at 6% (OF 400 or OG175C Unipectint by Degussa) was introduced dropwise to a solution of calcium chloride at 6% (m/v). The solution of pectin was introduced to the solution of calcium chloride via Tygon piping connected to a peristaltic pump (Microperpexe LKB Bromma). The solution was passed through a needle of 0.8 mm in diameter (21G, Nedus Terumo) to form drops of pectin which gelled instantly on contact with the calcium chloride (40 ml) and yielded beads of calcium pectinate. The beads were kept in the calcium chloride, with slow stirring, for 20 minutes.

The white beads not containing active ingredient (β-lactamases) were obtained starting out from a solution of amidated (OG 175C) or non-amidated (OF 400) pectin at 6%. For preparation of loaded beads the active ingredient (β-lactamases, penicillinases of type A extracted from Bacillus cereus by Sigma) was mixed in with the solution of pectin in a ratio of 3% (Vpa/Vpectin).

The resulting beads of calcium pectinate were then recovered by filtration, rinsed in distilled water, placed on a Petri dish and dried by kiln at 37° C. for 2 hours.

For reticulation in polyethylenimine the undried beads, recovered from the solution of $CaCl_2$ by filtration, were introduced to an aqueous solution of polyethylenimine (PEI) at 1% and were kept there for 20 min with gentle stirring.

The beads prepared from the non-amidated pectin OF 400 contained from 1 to 2.5 UI/beads and the beads prepared from amidated pectin OG175C contained from 1 to 5 UI/beads.

EXAMPLE 2

Stability of Beads

1. Operational Method.

The beads were prepared according to Example 1 with or without the reticulation stage; the duration of reticulation in PEI was 20 minutes in solutions of concentrations ranging from 0.6 to 1%.

The beads were placed either in phosphate buffer (PBS O,01M, pH 7.4), or in media simulating digestive juices (gastric and intestinal USP XXIV) and the disaggregation time was observed.

2. Results.

Figure 1:
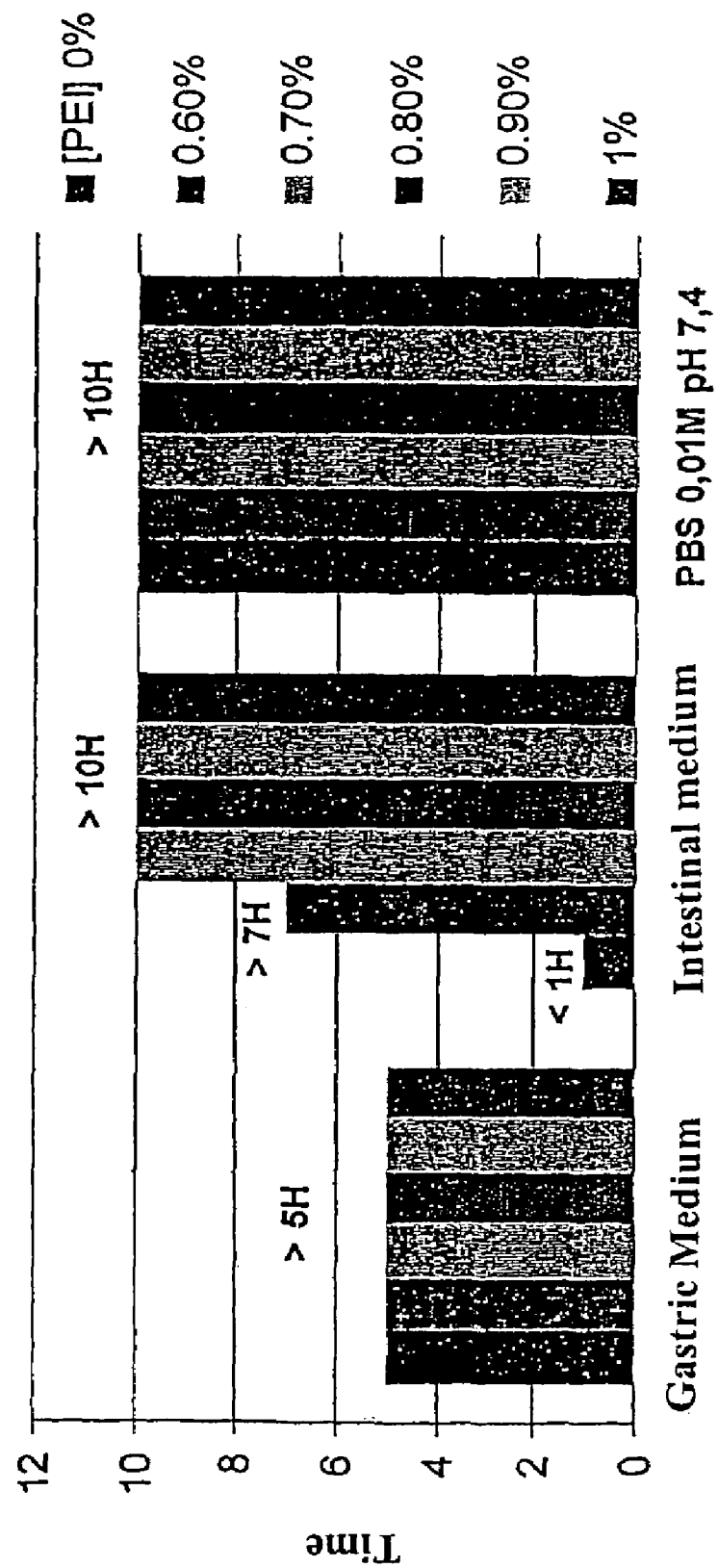
FIG. 1 shows the effect of reticulation with different concentrations of PEI (0.6; 0.7; 0.8; 0.9 and 1%) on the disaggregation time of amidated pectin beads, placed in three different media: PBS, 0.01 M, pH to 7.4; intestinal medium at pH of 6.8+0.1 UPS XXIV; gastric juice at pH of 1.1 USP XXIV.

These are given in FIG. 1.

The beads reticulated or not were stable in the PBS and in the gastric medium. However, the non-reticulated beads were unstable in the intestinal medium, whereas the beads according to the invention were stable for over 7 hours.

EXAMPLE 3

Morphological Characteristics of Beads

They are illustrated in FIGS. 2A to 2D.

The cuts show that the centre of the beads was full and dense. The surface shell corresponds to the PEI. The interior and exterior have different structures.

EXAMPLE 4

Release Kinetics in vitro

1. Operational Method.

Beads reticulated with two different concentrations of PEI (0.6 and 0.7%) were prepared according to Example 1 from amidated pectin and containing 5 UI/bead. They were left for 5 hours in intestinal medium USP XXIV at pH 6.8, then introduced to synthetic colonic medium at pH 6 including pectinolytic enzymes (Pectinex Ultra SPL).

The residual β-lactamase activity in the beads was measured over time by spectrophotometry in the presence of nitrocephine.

2. Results.

Figure 3:
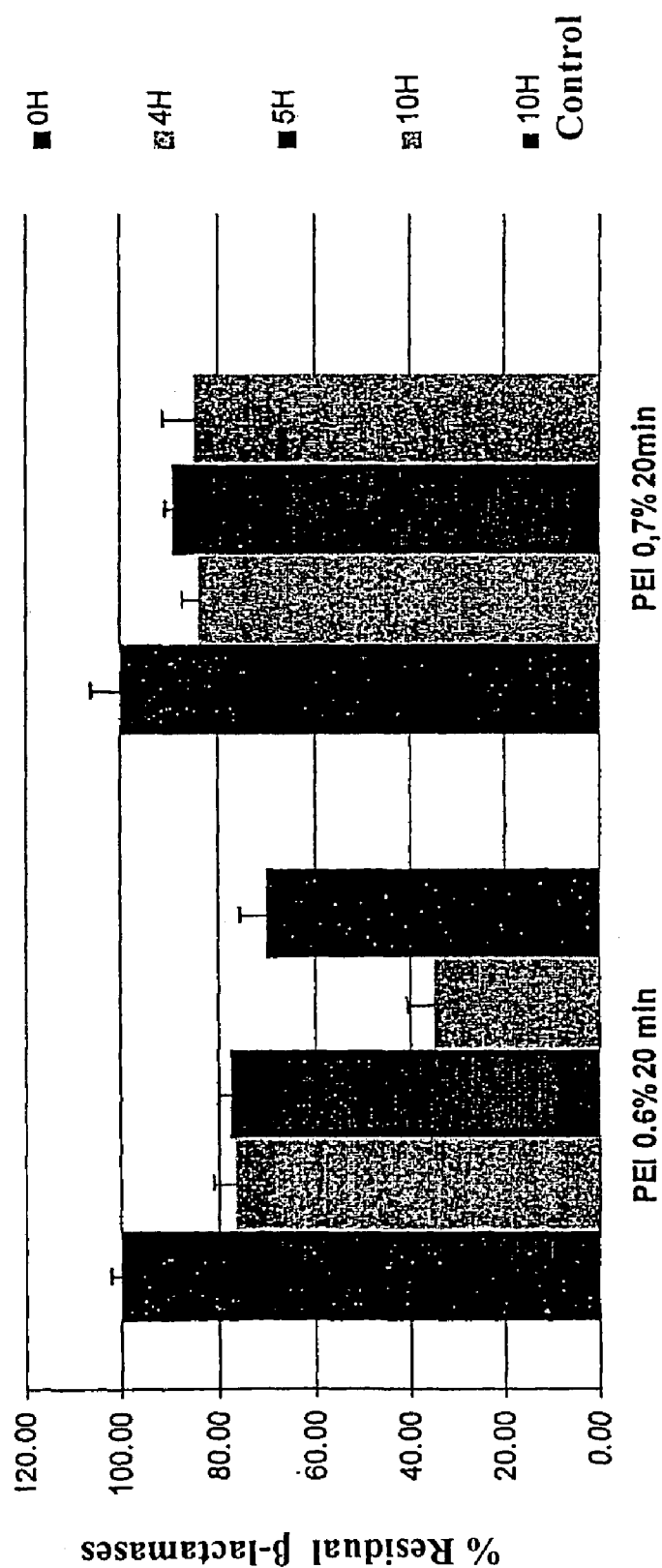
FIG. 3 illustrates the release of in vitro β-lactamases from reticulated amidated pectin beads prepared according to Example 1 with PEI concentrations of 0.6 and 0.7% and containing around 5 UI/bead, placed in intestinal medium USP XXIV then in colonic medium (HEPES buffer pH 6+pectinolytic enzymes).

They are illustrated in FIG. 3.

After 5 hours of incubation beads in intestinal medium ($T_{5H}$) less 25% of β-lactamase activity which they contain was released. The release becomes important in colonic medium under the action of pectinolytic enzymes (Tien), for the reticulated beads with 0.6% PEI, while the sample without pectinolytic enzymes ($T_{10H}$ control) had no significant modifications of β-lactamase activity. On the contrary, the beads reticulated with 0.7% PEI did not have their activity diminish after 5H in colonic medium.

Thus the concentration of PEI modifies the resistance of beads and plays on the release time of the active ingredients in colonic medium.

EXAMPLE 5

Release Kinetics in vivo

1. Operational Method.

This assay was performed on male mice CD1. The beads contain 4 UI/bead.

Gels containing 10 beads were administered per os to the mice. The stools were recovered at time periods of 0, 2 H, 3 H, 4 H, 5 H, 6 H, 7 H and 8 H and the dosage of β-lactamases in these stools was realized (assay conducted on 5 animals for each time). In addition, one mouse was sacrificed at times of 30 min, 2 H and 4 H so as to recover the beads in its digestive tract and observe their morphological modifications by scanning electron microscopy.

2. Results.

These are illustrated in FIGS. 4 to 7.

The beads arrived intact in the colon after around 3 hours' transit.

Figure 4:
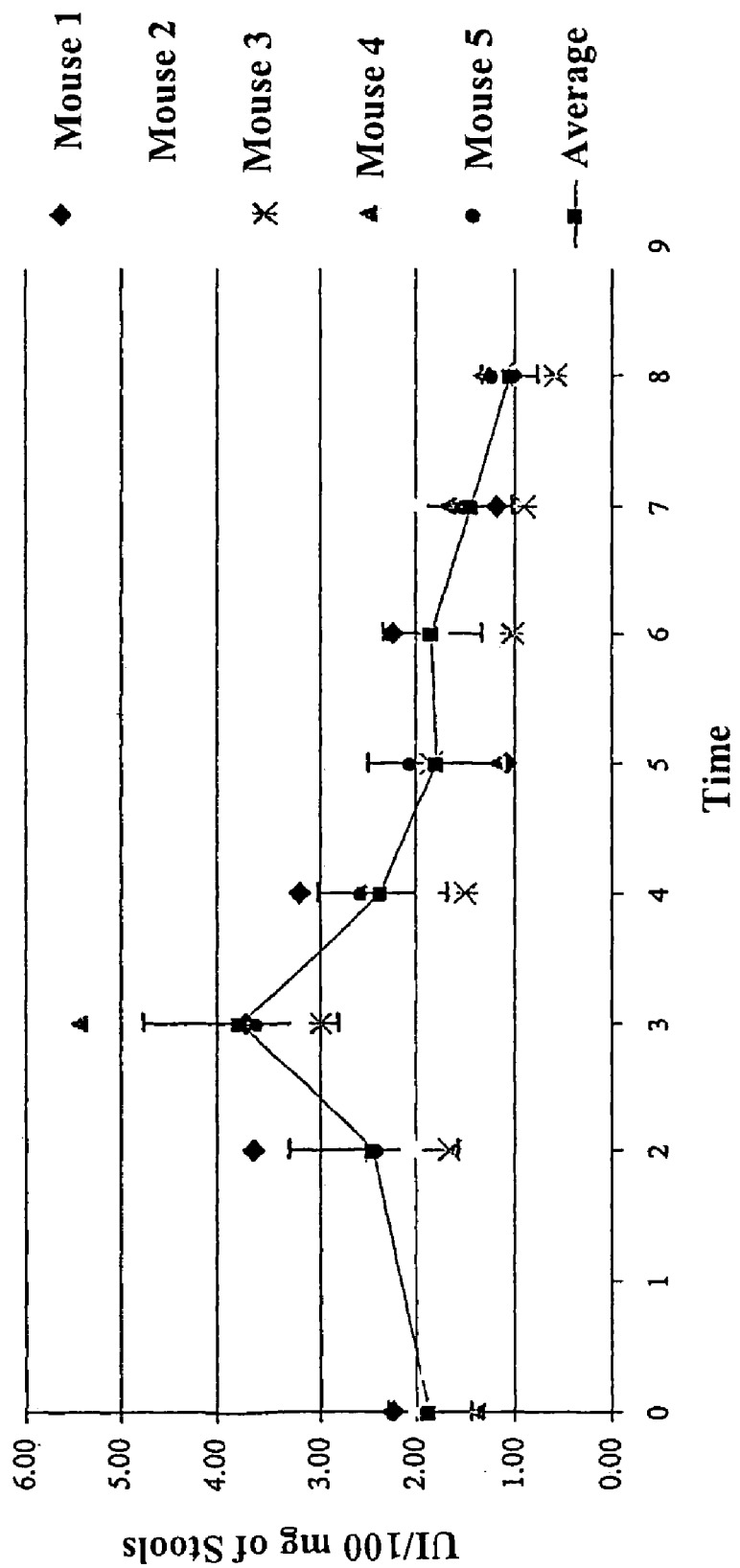
FIG. 4 illustrates the evolution of β-lactamase activity in the stools of mice as a function of time, after oral administration of reticulated pectin beads in PEI prepared according to Example 1 and containing 4.4 UI/bead.

The rate of β-lactamases released directly in the stools of mice gathered at different times after absorption of the beads orally shows that the basic β-lactamase activity is low at the outset. Two to 4 hours after administration there was a clear increase in this activity, corresponding to the transit of the beads (FIG. 4).

The photos taken by scanning electron microscopy show the integrity of the bead at different places of the digestive tract.

The structure is slightly fragile in the small intestine and the inside was completely destroyed at colonic level where the beads appeared carriers of a cavity.

Figure 2:
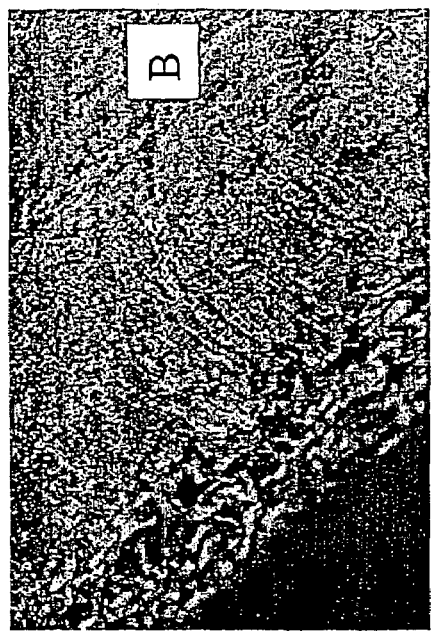
FIG. 2 illustrates the structure of beads containing β-lactamases at the rate of 4.4 UI/bead and reticulated for 20 minutes in PEI at 1% and observed by scanning electron microscopy.
Figure 2:
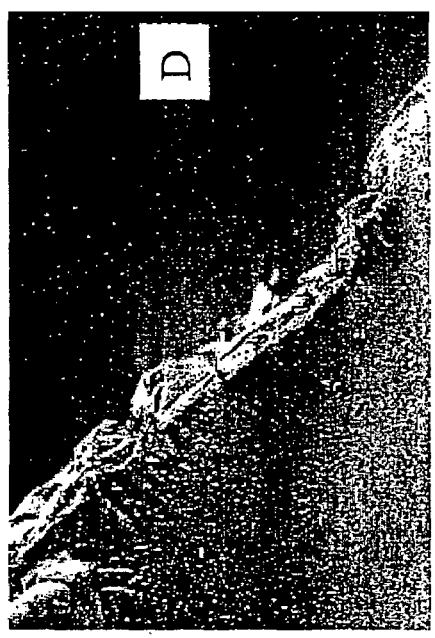
Figure 2:
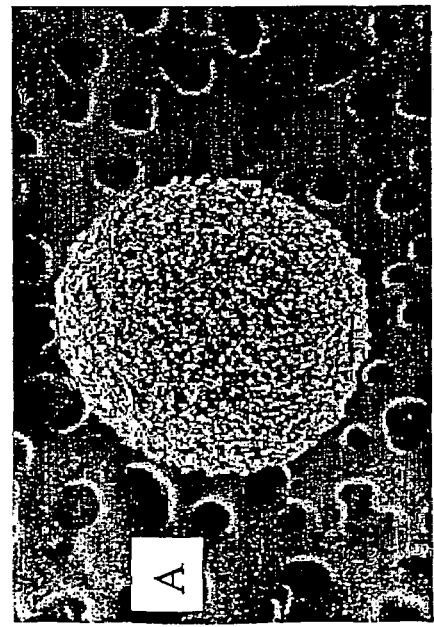
Figure 2:
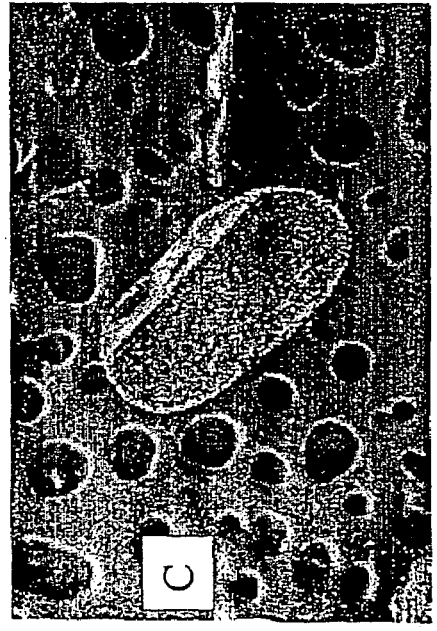
Figure 5:
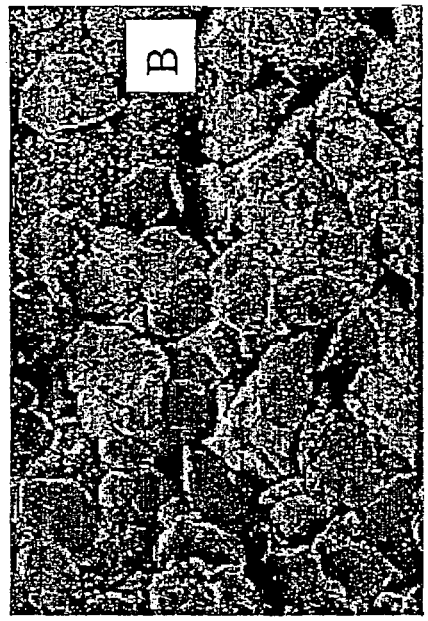
FIG. 5 illustrates the structure of beads containing β-lactamases at the rate of 4.4 UI/bead 30 minutes after in vivo administration. The beads are then in the stomach. A and B represent the whole beads and C and D the cut beads.
Figure 5:
Figure 5:
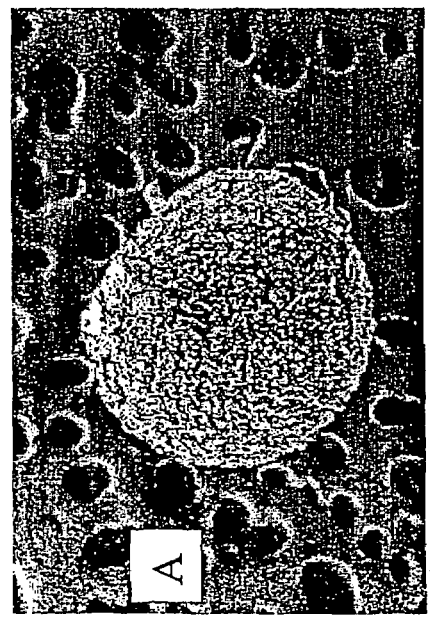
Figure 5:
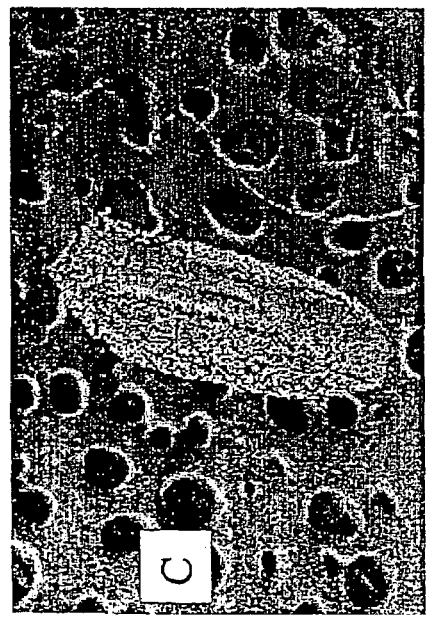
Figure 6:
FIG. 6 illustrates the structure of beads containing β-lactamases at the rate of 4.4 UI/bead 2 hours after in vivo administration. The beads are then in the small intestine. A and B represent the whole beads and C and D the cut beads.
Figure 6:
Figure 6:
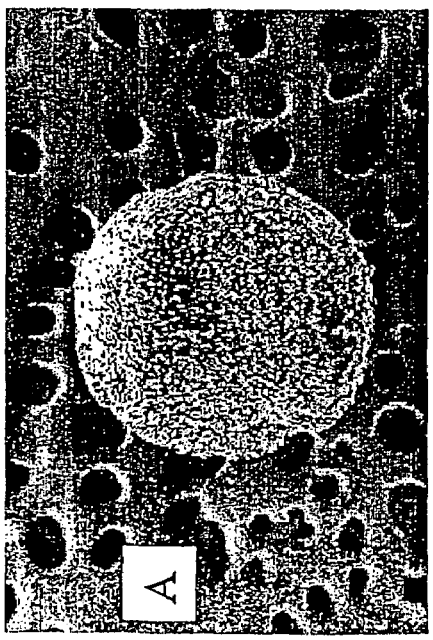
Figure 6:
Figure 7:
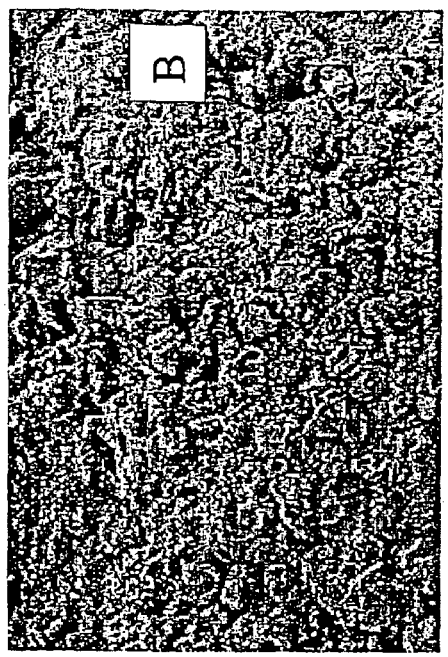
FIG. 7 illustrates the structure of beads containing β-lactamases at the rate of 4.4 UI/bead 4 hours after in vivo administration. The beads are then in the colon. A and B represent the whole beads and C and D the cut beads.
Figure 7:
Figure 7:
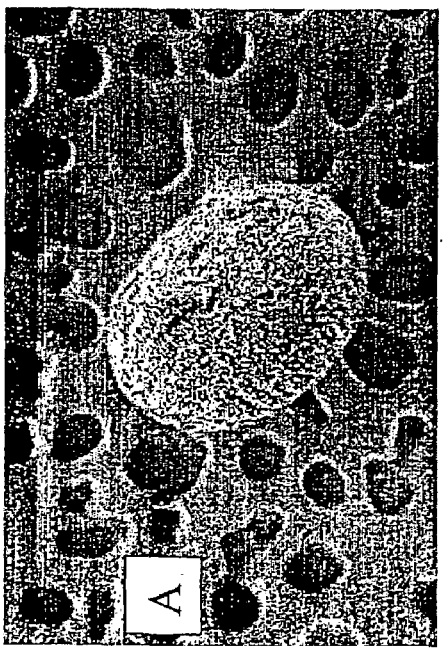
Figure 7:
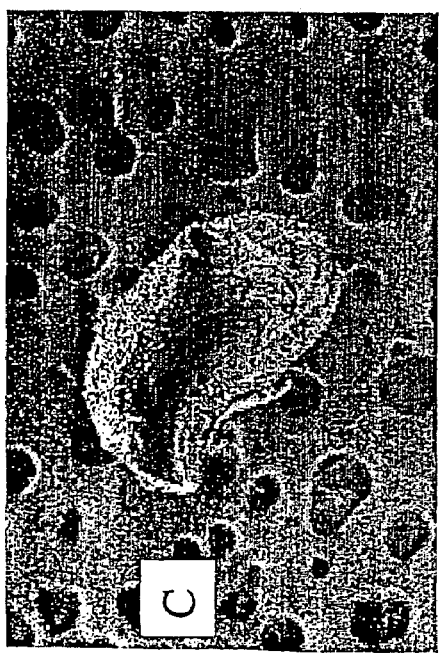

As illustrated in FIG. 5 the particles, having stayed in the stomach, looked very similar to those which had not undergone any treatment (FIG. 2). In effect the surface had the same rugged and irregular look (FIGS. 5A and 5B), owing to the presence of polyethylenimine, and the cross-section of the beads appeared uniform and dense (FIGS. 5C and 5D).

At the end of 2 h slight deformation of the beads became apparent (FIG. 6A), but the particles still had the same surface appearance (FIG. 6B) and a dense cross-section (FIG. 6C), even though they were made a little fragile by their stay in the small intestine (FIG. 6D).

On completion of transit, that is, 4 h after administration, the beads were in the colon; the external appearance of the particles was unchanged (FIG. 7A) with the same surface irregularities due to the polyethylenimine (FIG. 7B). Yet the cross-section of the beads was hollow (FIGS. 7C and 7D), due to the fact of degradation of the central network of calcium pectinate by the colonic pectinolytic enzymes. Finally, only the external shell formed by the polyethylenimine remained.

EXAMPLE 6

Encapsulation of Erythromycin Esterase 6.1 Production of a Soluble Fraction Containing Erythromycin Esterase 6.1.1. Operational Method The culture was made from the strain of *E. coli* C600 pIP1100 from the Pasteur Institute. The culture conditions were the following: inoculation of the Mueller-Hinton medium at 0.5% from a preculture of about 20 h, culture volumes of 200 or 400 mL in Erlenmeyer, fixed agitation at 150 rpm, temperature of 37° C.

A GOTS test helped establish that the strain produced much erythromycin esterase.

3.6 L of culture of *E. coli* C600 pIP1100 were concentrated according to the following protocol:

Centrifuging for 15 min at 3400 g

Recovery of pellet in potassium phosphate buffer 5 mM, pH 7.5, final volume 70 mL Second centrifuging of supernatant for 15 min at 3400 g Recovery of pellet in 20 mL of potassium phosphate buffer 5 mM, pH 7.5

Reuniting of pellets of the 2 centrifuges (around 100 mL)

Washing of pellets and centrifuging (10 min at 12,000 g)

Second centrifuging of supernatant (10 min 12,000 g)

Final volume of pellets recovered in the potassium phosphate buffer: 100 mL.

The erythromycin esterase was an intracellular enzyme. This is why its solubilization required the cells to be broken. This operation was carried out by ultrasonic extraction of centrifuging caps recovered in the potassium phosphate buffer 5 mM, pH 7.5 according to the protocol described hereinbelow.

Addition of 1% TritonX100 (v/v)

Cooling to 5° C.

Phonolysis 7 cycles of 1 min, initial temperature 5° C., maximal temperature 15° C., power: 100% (500 W, 20 kHz); temperature taken to 5° C. after each cycle Centrifuging for 10 min at 12,000 g Recovery of pellet in 10 mL of potassium phosphate buffer 5 mM, pH 7.5

Recovery and congealing of the supernatant (91 mL)=solution A.

The erythromycin esterase activity was evaluated by the microbiological dosage in the supernatant and in the insoluble substances (cellular debris) according to techniques known to the expert.

6.1.2. Results

The results are presented in Table 2.

TABLE 2

| | Diameter of inhibition (mm) | | | |
|---|---|---|---|---|
| Sample | T0 | T30 | T60 | T120 |
| Supernatant | 31 | 25 | 18 | — |
| after ultrasound | 21 | — | 18 | 14 |
| Pellet after | 30 | 28 | 24 | — |
| ultrasound | 22.5 | — | 19.5 | 19 |

The erythromycin esterase activity was evaluated from the diameter of inhibition.

The latter was 2 U/mL for the phonolysis supernatant and 1.5 U/mL for the phonolysis pellet (1 Unit (U)=1 μg of erythromycin degraded per min).

The balance of recuperation of the erythromycin esterase activity is presented in Table 3 hereinbelow.

TABLE 3

| Sample | Estimated Activity (U/mL) | Volume (mL) | Total estimated activity (U) |
|---|---|---|---|
| Supernatant after ultrasound | 2.0 | 92 | 184 |
| pellet after ultrasound | 1.5 | 10 | 15 |

The results clearly show that the essential element in the erythromycin esterase activity present has been solubilized in the phonolysis medium.

6.2 Encapsulation of Erythromycin Esterase 6.2.1. Operational Method

Encapsulation was achieved from the non-purified soluble fraction obtained after breaking the cells (solution A) according to the following protocol.

Solubilization of 0.5 g of pectin in 10 mL solution A to obtain a final concentration of pectin of 5% (solution B). The pectin was added very progressively with magnetic stirring so as not to cause too many abrupt variations in pH. The pH was maintained in the region of 7 by addition of a few drops of soda 1M.

Dispersion of the solution of pectin (solution B) dropwise by means of a peristaltic pump to 40 mL of $CaCl_2$ at 6%. The beads thus formed were kept in the $CaCl_2$ for 20 min, recovered by Büchner filtration then rinsed in demineralised water.

Reticulation of the beads by bath in a solution of PEI at 0.6% for 20 min with magnetic stirring.

Recovery of the reticulated beads by filtration.

The beads were dried at ambient temperature (20° C.). 567 beads were prepared in total with 6.1 mL of pectin/solution A mixture, for an activity of 12.2 U.

The dried beads were disaggregated in a buffer HEPES/NaCl/EDTA 1%.

6.2.2. Results

The erythromycin esterase activity present in the initial solution of pectin and that released in the disaggregation medium were dosed according to the same protocol as previously.

The results of the microbiological dosage are presented in Tables 4 and 5.

TABLE 4

| Sample | Average inhibition diameter (mm) |
| --- | --- |
| Pectin/Solution A (solution B) - T0 | 23 |
| Pectin/Solution A - T3h | 19 |
| Disaggregated beads - T0 | 24 |
| Disaggregated beads - T3h | 18 |

TABLE 5

| Sample | Estimated activity |
| --- | --- |
| Pectin (Solution B) | 2.4 |
| Disaggregated beads | 2.2 |

The results show that the activity measured in the presence of pectin (solution B) is 2.4 U, while the theoretical activity present should be around 12 U (6.1 mL at 2 U/mL, according to the dosage of erythromycin esterase in the phonolysis supernatant (Table 3).

The dosage of enzymatic activity of beads after disaggregation had been estimated at 2.2 U; it repressentsed 90% of the initial activity introduced to the beads.

These results help confirm unambiguously the presence of erythromycin esterase activity in the final fraction after encapsulation of the enzyme and disaggregation of the beads.

EXAMPLE 7

Encapsulation of DNA in the Calcium Pectinate Beads 7.1 Preparation of DNA

The active ingredient encapsulated here was a plasmid radiomarked with Phosphore 33. The radiomarking was done by means of the Nick Translation Kit N5500 from Amersham Biosciences according to the protocol described by the supplier.

7.2 Encapsulation 7.2.1. Operational Method

The encapsulated DNA was either in free form, or complexed with cationic lipids (Lipoplexe) or a cationic polymer (Polyplexe) according to the operational method described in Example 1.

For free DNA, around 5 µg of DNA radiomarked in solution in 750 µL of MilliQ water were introduced to 0.75 g of a pectin solution, amidated or not, at 10% so as to obtain a final concentration of pectin of 5%. In the case of the lipoplexes, 375 µL of an aqueous solution of radiomarked DNA were mixed with 375 µL of a suspension of cationic liposomes (N/P ratio of 10). The 750 µL of resulting lipoplexes were then mixed with 0.75 g of solution of pectin at 10% so as to obtain a final concentration of pectin of 5%.

In the case of polyplexes, 375 µL of an aqueous solution of radiomarked DNA was mixed with 375 µL of an aqueous solution of PEI 4 mM. 375 µL of the suspension of polyplexes thus obtained were then mixed with 0.75 g of pectin solution at 10% to provide a final concentration of pectin of 5%.

The beads of calcium pectinate encapsulating the free or complex DNA were then prepared from solutions obtained hereinabove according to the method described in Example 1.

The concentration of calcium chloride utilized here was 5% and that of PEI for reticulation was 0.6%.

7.2.2. Results

Figure 8:
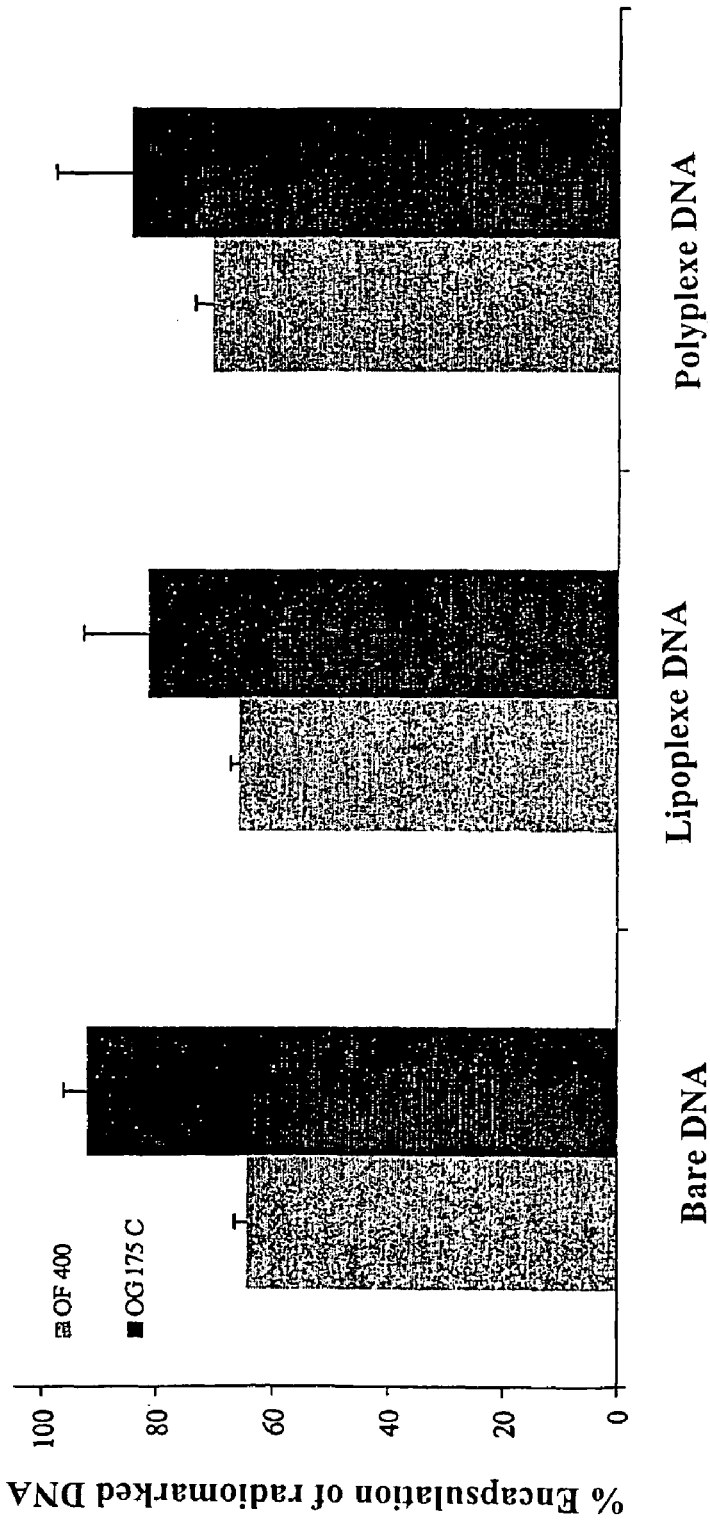
FIG. 8 illustrates encapsulation, in pectin beads, of free or complex plasmid DNA with cationic lipids (Lipoplexe) or cationic polymer (Polyplexe).

They are illustrated in FIG. 8 which shows the encapsulation yields of a plasmid DNA in amidated or non-amidated pectin beads.

The encapsulated DNA was either in free form, or complexed in cationic lipids (Lipoplexe) or a cationic polymer (Polyplexe).

The encapsulation yields of DNA varied between 60 and 90% according to the type of pectin used. They were generally more significant with amidated pectin. Complexing with lipids or a cationic polymer did not cause significant modifications to these yields, which remained relatively high.

The foregoing is illustrative of the present invention and is not to be construed as limiting thereof. The invention is defined by the following claims, with equivalents of the claims to be included therein. All cited references are hereby incorporated by reference in their entirety.

What is claimed is:

1. A drug delivery composition for oral administration, and colonic release, of an active agent, the composition comprising:
   a) an active agent capable of inactivating an antibiotic, wherein the active agent is an isolated enzyme capable of inactivating a β-lactam, macrolide, or quinolone antibiotic; and
   b) a pectinate suitable for administering the active agent to the colon, wherein said pectinate comprises a cationic pectinate salt in the form of a pectin bead which encloses the active agent.

2. The drug delivery composition of claim 1, wherein the active agent is an enzyme capable of inactivating a macrolide or quinolone antibiotic.

3. The drug delivery composition of claim 2, wherein the enzyme is an enzyme capable of inactivating a macrolide antibiotic, wherein said enzyme is erythromycin esterase.

4. The drug delivery composition of claim 1, wherein the pectin bead is reticulated by a cationic polymer.

5. The drug delivery composition of claim 1, wherein the pectinate salt is a calcium pectinate.

6. The drug delivery composition of claim 1, wherein the pectinate is an amidated pectinate.

7. The drug delivery composition of claim 1, wherein the active agent is an enzyme capable of inactivating a β-lactam antibiotic, wherein said enzyme is β-lactamase.

8. The drug delivery composition of claim 1, further comprising:
   c) a second active agent, wherein the second active agent is selected from the group consisting of an antibiotic, an anti-inflammatory, an anti-histamine, an anti-cholinergic, an antiviral, an antimitotic, a peptide, a protein, an immunosuppressive agent, and a bacteria.

9. A method of reducing the concentration of an antibiotic in the colon of a patient, the method comprising orally administering the drug delivery composition of claim 1 to a patient in need thereof wherein said patient has been, is being, or will be administered an antibiotic, wherein said antibiotic is selected from the group consisting of a β-lactam, a macrolide, and a quinolone antibiotic.

10. The method of claim 9, wherein the active agent in the drug delivery composition is an enzyme capable of inactivating a macrolide or quinolone antibiotic.

11. The method of claim 10, wherein the enzyme is an enzyme capable of inactivating a macrolide antibiotic, wherein said enzyme is erythromycin esterase.

12. The method of claim 11, wherein the pectin bead is reticulated by a cationic polymer.

13. The method of claim 11, wherein the pectinate salt is a calcium pectinate.

14. The method of claim 11, wherein the pectinate is an amidated pectinate.

* * * * *